United States Patent [19]

Umansky et al.

[11] Patent Number: 5,476,981
[45] Date of Patent: Dec. 19, 1995

[54] OXIDATIVE DEHYDROGENATION OF HYDROCARBONS WITH SOLID SUPERACID CATALYST

[75] Inventors: Benjamin S. Umansky, Chalfonte, Del.; Chao-Yang Hsu, Media, Pa.

[73] Assignee: Sun Company, Inc. (R&M), Philadelphia, Pa.

[21] Appl. No.: 174,733

[22] Filed: Dec. 29, 1993

[51] Int. Cl.⁶ ................................ C07C 5/32; C07C 2/84
[52] U.S. Cl. .................... 585/656; 585/658; 585/661; 585/444; 585/445
[58] Field of Search ........................ 585/622, 440, 585/654, 658, 660, 661, 662, 663, 621, 618, 623, 624, 625, 627, 444, 445

[56] References Cited

U.S. PATENT DOCUMENTS

| | | |
|---|---|---|
| 3,113,984 | 12/1963 | Gosselin et al. . |
| 3,497,564 | 2/1970 | Allen et al. ............................. 260/650 |
| 3,725,494 | 4/1973 | Ripley ................................. 260/680 E |
| 4,652,690 | 3/1987 | Lee . |
| 4,918,041 | 4/1990 | Hollstein et al. . |
| 4,956,519 | 9/1990 | Hollstein et al. . |

OTHER PUBLICATIONS

Manassen et al., "Organic Polymers, Correlation between Their Structure and Catalytic Activity in Heterogeneous Systems. I. Pyrolyzed Polyacrylonitrile and Polycyanoacetylene" *J. Am. Chem. Soc.*, 87:12, 2671–2677 (1965).

*Primary Examiner*—Asok Pal
*Assistant Examiner*—Bekir L. Yildirim
*Attorney, Agent, or Firm*—Q. Todd Dickinson; Stephen T. Falk

[57] ABSTRACT

Solid superacid catalyst, for example sulfated zirconia, is used in the oxidative dehydrogenation of saturated or partially saturated hydrocarbons, for example the conversion of isobutane to isobutylene in the presence of an oxygen-containing oxidizing agent at reaction conditions typically including temperatures from 500 to 1,000 degrees Fahrenheit, superatmospheric pressures, and oxygen/alkane molar ratios from 0.2 to 20. Performance of a metal-oxide or metal-hydroxide oxidative dehydrogenation catalyst may be enhanced by pretreating a solid superacid or other catalyst containing metal oxides or hydroxides at a carbonizing temperature with an organic material, for example an oxygen-containing organic material, to form a carbonaceous layer on the surface thereof prior to use of the catalyst in oxidative dehydrogenation.

13 Claims, No Drawings

5,476,981

OXIDATIVE DEHYDROGENATION OF HYDROCARBONS WITH SOLID SUPERACID CATALYST

BACKGROUND OF THE INVENTION

The oxidative dehydrogenation of alkane hydrocarbons or alkyl-containing hydrocarbons to olefinic structures is currently of increasing importance, both for reasons of energy and thermodynamics. Over the past three decades work has appeared from different laboratories describing a group of catalysts such as alumina and various metal phosphates, which are very selective for oxidative dehydrogenation of alkylaromatics such as ethylbenzene to styrene. During this time, evidence has been accumulated that the active site for these catalysts is actually a coke layer which is initially deposited on the surface. The carbon molecular sieves or active carbon have also shown significant activity for these oxidative dehydrogenation reactions. See J. Manassen et al, "Action of Zirconium Phosphate as a Catalyst for the Oxydehydrogenation of Ethylbenzene to Styrene", *J. Amer. Chem. Soc.*, 87, 2671 (1965), G. Emig et al, "Organic Polymers. Correlation Between Their Structure and Catalytic Activity in Heterogeneous Systems. I. Pyrolyzed Polyacrylonitrile and Polycyanoacetylene" *J. of Catalysis*, 84, 15 (1983) and C. C. Grunewald et al, "Oxidative Dehydrogenation of Ethylbenzene to Styrene Over Carbon-Based Catalysts", *J. Molecular Catalysis*, 58, 227 (1990).

C. S. Lee U.S. Pat. No. 4,652,690, Mar. 24, 1987, discloses that carbon molecular sieves are catalysts for oxidative dehydrogenation of ethylbenzene to styrene in the presence of oxygen and steam at temperatures of 300° to 400° C. and unspecified pressure.

K. F. Gosselin et al U.S. Pat. No. 3,113,984, Dec. 10, 1963 discloses that carbon molecular sieves are catalysts for oxidative dehydrogenation of alkanes at 900° to 950° F. and unspecified pressure. Since the reaction was done in a Pyrex tube, atmospheric or lower pressure was apparently used.

Aluminum oxide has also been used as a catalyst for oxidative dehydrogenation of hydrocarbons, in T. G. Alkhazov et al, "Oxidative Dehydrogenation of Alkyl Aromatic Hydrocarbons on Aluminum Catalysts. The Nature of the Process of Oxidative Dehydrogenation of Ethylbenzene on Aluminum Oxide", Kinetics *i Katalyz.*, Vol. 14, No. 5, pp 1182–1188 (1973); this reference discloses that aluminum oxide is a catalyst for oxidative dehydrogenation of ethylbenzene to styrene in the presence of air at a temperature of 500° C. and subatmospheric, e.g. 10 torr., pressure.

Although oxidative dehydrogenation usually involves the use of a catalyst, and is therefore literally a catalytic dehydrogenation, oxidative dehydrogenation is distinct from what is normally called "catalytic dehydrogenation" in that the former involves the use of an oxidant, and the latter does not. In the disclosure herein, "oxidative dehydrogenation", though employing a catalyst, will be understood as distinct from so-called "catalytic dehydrogenation" processes in that the latter do not involve the interaction of oxygen in the feed with the hydrocarbon feed. Solid superacids have been disclosed as catalysts for dehydrogenation of hydrocarbons, though not for oxidative dehydrogenation of hydrocarbons. E. J. Hollstein et al U.S. Pat. Nos. 4,918,041, Apr. 17, 1990 and 4,956,519, Sep. 11, 1990, disclose that certain solid superacid compositions, for example sulfated zirconia containing iron and manganese, are suitable for catalyzing the dehydrogenation or partial oxidation of hydrocarbons; no specific dehydrogenation or partial oxidation reactions, nor any conditions for such reactions, are disclosed.

DESCRIPTION OF THE INVENTION

This invention provides an improved process for the oxidative dehydrogenation of light alkanes to olefins, for example ethane to ethylene, propane to propylene, butanes to butylenes and pentanes to pentenes, or of alkylaromatic compounds such as ethylbenzene to styrene, and the like, using solid superacid catalysts.

OXIDATIVE DEHYDROGENATION WITH SOLID SUPERACID CATALYST

In the process according to the invention, light alkanes or alkylaromatic compounds together with molecular oxygen, are passed through for example a fixed bed reactor containing a solid superacid catalyst under reaction conditions to give olefins, carbon oxides and water as products. Examples of the solid superacids which may be used as catalysts for oxidative dehydrogenation of alkanes according to the invention are sulfated zirconia, sulfated titania, sulfated iron oxide, sulfated alumina, halogenated alumina, etc. These catalysts can be used alone or with one or more metals to enhance the superacidity, as disclosed in E. J. Hollstein et al U.S. Pat. Nos. 4,918,041 (1990) and 4,956,519 (1990), referred to above, the disclosures of which are hereby incorporated by reference.

The process according to the invention uses as an oxidizing agent, oxygen, air or other oxygen-containing mixtures. Sulfur dioxide, hydrogen sulfide and steam, together with oxygen or oxygen containing mixtures also can be used. Any suitable pressure may be used, but superatmospheric pressures, preferably higher than 100 psia, and more preferably between 200 psia and 400 psia, are used in order to obtain substantial yields, since at atmospheric pressure, no substantial oxidative dehydrogenation occurs. The reaction temperature range is preferably between 500° F. and 1000° F., more preferably between 600° F. and 800° F. The metals are selected from the groups VB, VIB, VIIB, VIII, IIB, IIIA, IVA and VA, preferably V, Cr, Mn, Fe, Zn, Co, Sn, Pb, Ca and Sb. The LHSV (liters/hour) for the light alkane feed is preferably between 0.5 to 6, more preferably between 1 to 3. The $O_2$/alkane molar ratio is preferably in the range from about 0.2 to about 20, more preferably between 2 to 7. An advantage of the process of the invention, using solid superacid catalysts, as compared with use of active carbon as catalyst in the prior art oxidative dehydrogenation of alkanes or alkylaromatic compounds, is that the catalyst used in the process of the invention can be periodically regenerated. As the solid superacid catalyst is used in the process of the invention, its activity may initially be enhanced by the formation of active carbon sites on the surface of the catalyst as a result of carbonizing reactions. After prolonged use, however, the activity of the catalyst is reduced as a result of further deposits of carbon on the catalyst surface. After such deactivation has occurred, the activity of the catalyst can be restored by regeneration in which carbon is burned from the surface of the superacid catalyst, an advantageous procedure which is not feasible with the active carbon catalysts of the prior art.

PREFORMED ACTIVE CARBON SITES

The process of the invention also makes possible a procedure in which a solid metal-oxide or metal-hydroxide catalyst, such as a solid superacid catalyst, used in the oxidative dehydrogenation step, has a preformed layer of carbonaceous material thereon which provides active carbon sites on the surface of the catalyst; the active carbon sites enhance the ability of the catalyst to catalyze oxidative dehydrogenation.

The carbonaceous layer is typically formed on the catalyst surface by contacting the solid catalyst with an organic compound or compounds which decompose under the conditions employed to form a carbonaceous deposit on the catalyst. The conditions used in such pretreatment are different from the conditions used in the subsequent oxidative dehydrogenation. The difference between the conditions in the respective steps may reside in the organic material contacted with the catalyst in the respective steps, or in one or more of the temperature, pressure or other parameters of the respective steps.

In this embodiment, the process parameters may be varied between the pretreatment and the oxidative dehydrogenation steps, in order to optimize the results of each step in relationship to its objective, the objective of the pretreatment being to form catalytically active carbon sites on the catalyst, and the objective of the oxidative dehydrogenation step being to achieve the desired dehydrogenation of the hydrocarbon starting material. By routine experimentation within the ability of the person skilled in the art, these functions may be optimized for a given situation.

PRETREATMENT MATERIAL

In one embodiment of the invention, during the pretreatment, a material different from the compound to be oxidatively dehydrogenated is contacted with the catalyst, and during the oxidative dehydrogenation, the contact of the catalyst with such material is discontinued and the contact of the catalyst, now bearing active carbon sites, with the starting material for the oxidative dehydrogenation is begun. In the case of oxidatively dehydrogenating an alkane, the pretreatment material may be, for example, an aromatic compound such as benzene or a substituted benzene. In the case of oxidatively dehydrogenating an alkylaromatic compound, the pretreatment material may be for example another aromatic compound such as an oxygen-containing aromatic compound, for example a phenolic compound or compounds or an anthraquinone compound or compounds; such oxygen containing aromatic compounds have been identified in the products of the oxidative dehydrogenation step, indicating that they may be precursors to the formation of active carbon sites on the catalyst. Other types of organic materials may be used in the pretreatment.

CATALYSTS PRETREATED

In the embodiment of the invention wherein a solid metal-oxide or metal-hydroxide catalyst is pretreated to form active carbon sites and the pretreated catalyst containing active carbon sites is then used as catalyst in oxidative dehydrogenation, the catalyst may be a solid superacid or it may be another metal-oxide or metal-hydroxide catalyst such as aluminum oxide or other known catalyst for oxidative dehydrogenation of hydrocarbons.

The formation of active carbon sites on the catalyst by pretreatment prior to oxidative dehydrogenation according to this embodiment of the invention provides advantages over the formation of active carbon sites during the early stages of oxidative dehydrogenation of a starting material by decomposition of a portion of the starting material, in that in the pretreatment the formation of active carbon sites may be conducted at conditions providing optimum results for the pretreatment, and in that superior results from the presence of active carbon sites can be obtained from the beginning of the oxidative dehydrogenation step.

After the pretreated catalyst has become deactivated through the accumulation of further carbonaceous deposits during the oxidative dehydrogenation, the catalyst may be regenerated by burning off at least the excess carbon on the deactivated catalyst.

The following examples illustrate the invention.

EXAMPLE 1

5 ml of a superacid, a sulfated (4% sulfate) zirconia containing 1.5% Fe and 0.5% Mn, was used as a catalyst for the oxidative dehydrogenation of isobutane in a ½" O. D. fixed reactor. The principal product was isobutylene; propylene was also produced as a result of partial decomposition of the alkane feed in addition to dehydrogenation thereof. Oxygen in the feed is converted to carbon oxides; partial oxidation products such as aldehydes, ketones and alcohols are minimized. The reaction conditions and the results obtained in each case are shown in Table 1.

TABLE 1

| Temperature (C.) | 425 | 400 | 350 |
|---|---|---|---|
| Pressure (psia) | 250 | 240 | 450 |
| LHSV (1/Hr.): | 3 | 3 | 3 |
| GHSV (1/Hr.): | 2000 | 2000 | 2000 |
| [$O_2/N_2$ (4% $O_2$)] | | | |
| i-$C_4H_{10}$ Conversion: | 19.3% | 22% | 25% |
| Selectivity to i-$C_4H_8$: | 37.3% | 45.5% | 36%1 |
| Selectivity to $C_3H_6$: | 20.7% | 27.3% | 29% |
| Selectivity to $CO_x$: | 28% | 18.2% | 27% |
| Selectivity to $C_4-,+$: | 14% | 9.1% | 8% |

EXAMPLE 2

5 ml of a superacid, a sulfated (4% sulfate) zirconia containing 2% Ni and 0.7% W, was used as catalyst for oxidative dehydrogenation of isobutane in a ½" O. D. fixed reactor, under conditions generally similar to those in Example 1, except for the difference in the catalyst. The reaction conditions and the results obtained in each case are shown in Table 2:

TABLE 2

| Temperature (C.): | 425 | 400 |
|---|---|---|
| Pressure (psia): | 350 | 350 |
| LHSV (1/Hr.) | 3 | 3 |
| GHSV (1/Hr.) | 2000 | 2000 |
| [$O_2/N_2$(4% $O_2$)] | | |
| i-$C_4H_{10}$ Conversion: | 27% | 12.5% |
| Selectivity to i-$C_4H_8$: | 37% | 34% |
| Selectivity to $C_3H_6$: | 15.2% | 15% |
| Selectivity to $CO_x$: | 33% | 31% |

Table 1 shows that at oxidative dehydrogenation temperatures of 350 to 425 C. (662 to 817 F.) and pressures of 240 to 450 psia, sulfated zirconia catalyst containing iron and manganese oxides or hydroxides gives conversions of isobutane of about 19 to 25 percent and selectivities of about 36 to 46 percent to isobutene. Table 2 shows that at oxidative dehydrogenation temperatures of 400 to 425 C. and pressure of 350 psia, sulfated zirconia catalyst containing nickel and tungsten oxides or hydroxides gives conversions of isobutane of about 12 to 27 and selectivities of about 34 to 37 percent to isobutene.

The process of the invention is preferably applied to alkanes or mixtures thereof containing 1 to 7 carbon atoms per molecule, though the process is capable of oxidatively dehydrogenating alkanes having greater numbers of carbon atoms. The alkyl groups of alkylaromatics such as ethylbenzene and the like may also be oxidatively dehydrogenated by the process of the invention. In the light of the present specification, the person skilled in the art can apply the process of the invention to oxidative dehydrogenation of other alkyl-group-containing structures. The manner of applying the invention to alkylaromatic compounds such as ethylbenzene to form unsaturated compounds such as styrene is similar to that of applying the invention to the oxidative dehydrogenation of alkanes such as isobutane to form unsaturated compounds such as isobutylene. However, the optimum conditions for use in conjunction with alkyldromatics may differ in ways within the skill of the art to determine from the optimum conditions for use in conjunction with alkanes.

The invention claimed is:

1. Process for oxidative dehydrogenation of an alkane or alkylaromatic compound which comprises contacting said alkane or alkylaromatic compound with oxygen and a solid superacid catalyst under oxidative dehydrogenation conditions to convert said alkane or alkylaromatic compound to an alkene or alkenylaromatic compound.

2. Process according to claim 1 wherein said oxidative dehydrogenation conditions include a temperature in the range from about 500° F. to about 1000° F., a pressure higher than about 100 psia, and an $O_2$/hydrocarbon molar ratio in the range from about 0.2 to 20.

3. Process according to claim 2 wherein said temperature is in the range from about 600° F. to about 800° F., said pressure is in the range from about 200 psia to about 400 psia, and said $O_2$/hydrocarbon molar ratio is in the range from about 2 to about 7.

4. Process according to claim 1 wherein said solid superacid catalyst comprises a sulfated oxide or hydroxide of a group VB, VIB, VIIB, VIII, IIB, IIIA, IVA or VA metal.

5. Process according to claim 4 wherein said metal is vanadium, chromium, manganese, iron, zinc, cobalt, tin, lead, gallium, antimony, tungsten or nickel.

6. Process according to claim 5 wherein said metal is iron.

7. Process according to claim 1 wherein said catalyst comprises sulfated oxide or hydroxide of iron and manganese.

8. Process according to claim 1 wherein said catalyst comprises sulfated oxide or hydroxide of nickel and tungsten.

9. Process according to claim 1, 2, 3, 4, 5, 6, 7 or 8 wherein said hydrocarbon is an alkane.

10. Process for oxidatively dehydrogenating an alkane or alkylaromatic compound which comprises contacting said alkane or alkylaromatic compound with a catalyst containing solid superacid having preformed active carbon sites on the surface thereof under oxidative dehydrogenation conditions.

11. Process for oxidatively dehydrogenating an alkane or alkylaromatic compound which comprises (1) pretreating a catalyst containing solid superacid by contact with an organic material under conditions to deposit carbonaceous material providing active carbon sites on the surface of said catalyst, and (2) contacting said catalyst containing active carbon sites with said alkane or alkylaromatic compound under oxidative dehydrogenation conditions.

12. Process according to claim 11 wherein said organic material comprises an aromatic compound other than said alkylaromatic compound.

13. Process according to claim 11 wherein said organic material is an oxygen-containing aromatic compound.

* * * * *